US00PP33145P2

(12) United States Plant Patent
van Voorst

(10) Patent No.: US PP33,145 P2
(45) Date of Patent: Jun. 8, 2021

(54) *ALSTROEMERIA* PLANT NAMED 'ZAPRICHARMI'

(50) Latin Name: *Alstroemeria hybrida*
Varietal Denomination: ZAPRICHARMI

(71) Applicant: Aart van Voorst, Hillegom (NL)

(72) Inventor: Aart van Voorst, Hillegom (NL)

(73) Assignee: Van Zanten Breeding B.V., Rijsenhout (NL)

( * ) Notice: Subject to any disclaimer, the term of this patent is extended or adjusted under 35 U.S.C. 154(b) by 0 days.

(21) Appl. No.: 16/873,545

(22) Filed: Apr. 30, 2020

(51) Int. Cl.
*A01H 5/02* (2018.01)
*A01H 6/56* (2018.01)

(52) U.S. Cl.
USPC ..... Plt./309

(58) Field of Classification Search
USPC ..... Plt./309
CPC ... A01H 5/02; A01H 5/00; A01H 6/56; A01H 6/564
See application file for complete search history.

(56) References Cited

PUBLICATIONS

Florium.ua *Alstroemeria* Charmelita White Zapricharmi Google Translate, retrieved on Oct. 1, 2020, retrieved from the Internet at https://translate.google.com/translate?hl=en&sl=uk&u=https://florium.ua/ua/alstroemeria/volin/page/2/&prev=search&pto=aue, 5 pp. (Year: 2020).*

* cited by examiner

*Primary Examiner* — June Hwu
(74) *Attorney, Agent, or Firm* — C. Anne Whealy

(57) ABSTRACT

A new and distinct cultivar of *Alstroemeria* plant named 'ZAPRICHARMI', characterized by its compact, upright to outwardly spreading and uniformly mounded plant habit; moderately vigorous growth habit and moderate growth rate; numerous small white-colored flowers; and excellent container and garden performance.

2 Drawing Sheets

Figure 1:
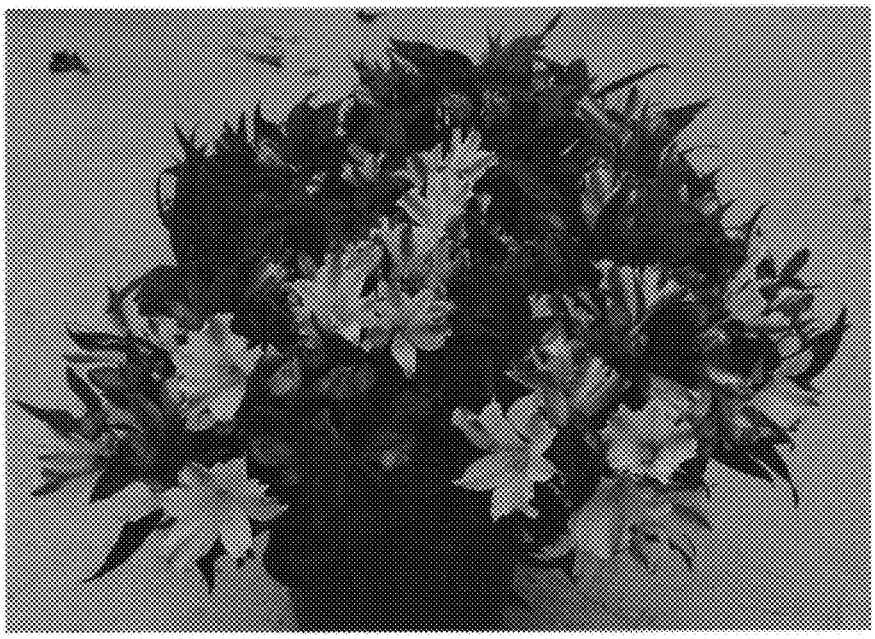

Botanical designation: *Alstroemeria hybrida.*
Cultivar denomination: 'ZAPRICHARMI'.

STATEMENT REGARDING PRIOR DISCLOSURES BY INVENTOR/APPLICANT

An European Community Plant Breeder's Rights application for the instant plant was filed by the Assignee, Van Zanten Breeding B.V. of Aalsmeer, The Netherlands, on Aug. 16, 2019, application number 2019/1991. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor/Applicant. Inventor/Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Alstroemeria* plant, botanically known as *Alstroemeria hybrida*, commercially used as a potted and garden-type *Alstroemeria*, and hereinafter referred to by the name 'ZAPRICHARMI'.

The new *Alstroemeria* plant is a product of a planned breeding program conducted by the Inventor in Rijsenhout, The Netherlands. The objective of the breeding program is to create new potted *Alstroemeria* plants with uniform plant habit, freely flowering habit, attractive leaf and flower coloration and good garden performance.

The new *Alstroemeria* plant originated from a cross-pollination made by the Inventor in Rijsenhout, The Netherlands in June, 2010 of a proprietary *Alstroemeria hybrida* selection identified as code number 72736-1, not patented, as the female, or seed, parent with a proprietary *Alstroemeria hybrida* selection identified as code number 94913-1, not patented, as the male, or pollen, parent. The new *Alstroemeria* plant was discovered and selected by the Inventor as a single flowering plant from within the progeny of the stated cross-pollination in a controlled greenhouse environment in Rijsenhout, The Netherlands in May, 2011.

Asexual reproduction of the new *Alstroemeria* plant by rhizome divisions in a controlled greenhouse environment in Rijsenhout, The Netherlands since September, 2011 has shown that the unique features of this new *Alstroemeria* plant are stable and reproduced true to type in successive generations.

SUMMARY OF THE INVENTION

Plants of the new *Alstroemeria* have not been observed under all possible combinations of environmental conditions and cultural practices. The phenotype may vary somewhat with variations in environmental conditions such as temperature and light intensity without, however, any variance in genotype. The following traits have been repeatedly observed and are determined to be the unique characteristics of 'ZAPRICHARMI'. These characteristics in combination distinguish 'ZAPRICHARMI' as a new and distinct *Alstroemeria* plant:

1. Compact, upright to outwardly spreading and uniformly mounded plant habit.
2. Moderately vigorous growth habit and moderate growth rate.
3. Numerous small white-colored flowers.
4. Excellent container and garden performance.

Plants of the new *Alstroemeria* can be compared to plants of the female parent selection. Plants of the new *Alstroemeria* differ from plants of the female parent selection primarily in flower size as plants of the new *Alstroemeria* have smaller flowers than plants of the female parent selection.

Plants of the new *Alstroemeria* can be compared to plants of the male parent selection. Plants of the new *Alstroemeria* differ from plants of the male parent selection primarily in flower color as plants of the new *Alstroemeria* have white-colored flowers whereas plants of the male parent selection have yellow-colored flowers. In addition, flowers of plants of the new *Alstroemeria* are smaller than flowers of plants of the male parent selection.

Plants of the new *Alstroemeria* can be compared to plants of *Alstroemeria hybrida* 'Zalsacharm', disclosed in U.S. Plant Pat. No. 26,959. In side-by-side comparisons, plants of the new *Alstroemeria* differ primarily from plants of 'Zalsacharm' in plant habit as plants of the new *Alstroemeria* are more compact than plants of 'Zalsacharm'. In addition, plants of the new *Alstroemeria* are suitable as container and landscape plants whereas plants of 'Zalsacharm' are suitable as cut flower plants.

BRIEF DESCRIPTION OF THE PHOTOGRAPHS

The accompanying colored photographs illustrate the overall appearance of the new *Alstroemeria* plant showing the colors as true as it is reasonably possible to obtain in colored reproductions of this type. Colors in the photographs may differ slightly from the color values cited in the detailed botanical description which accurately describe the colors of the new *Alstroemeria* plant.

The photograph on the first sheet (FIG. 1 of 2) is a side perspective view of a typical flowering plant of 'ZAPRICHARMI' grown in a container.

Figure 2:
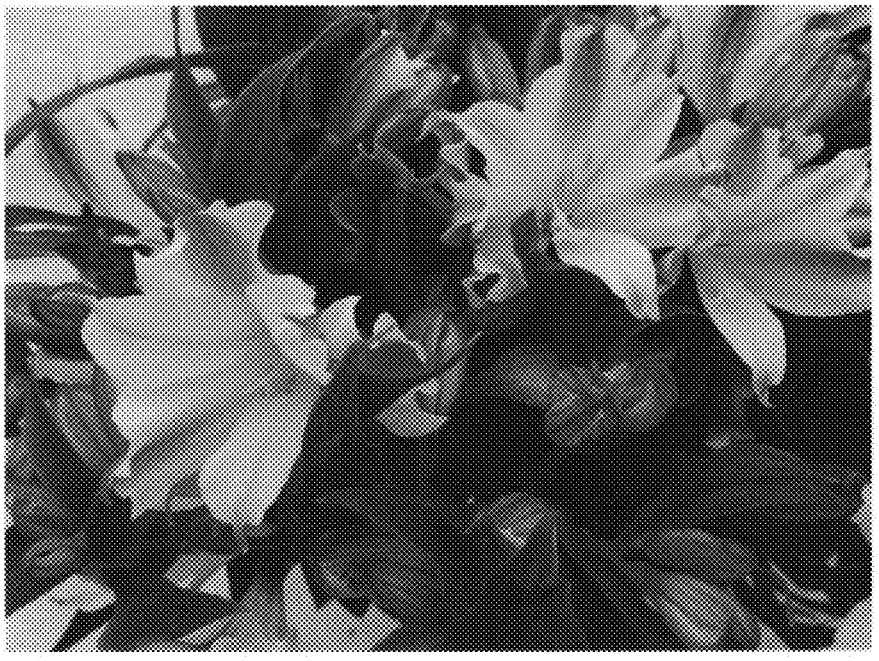

The photograph on the second sheet (FIG. 2 of 2) is a close-up view of typical leaves and flowers of 'ZAPRICHARMI'.

DETAILED BOTANICAL DESCRIPTION

The aforementioned photographs and following observations and measurements describe plants of the new *Alstroemeria* grown during the spring in 14-cm containers in a glass-covered greenhouse in Rijsenhout, The Netherlands. During the production of the plants, day temperatures ranged from 15° C. to 25° C., night temperatures ranged from 10° C. to 15° C., soil temperatures averaged 14° C. and light levels averaged 5,000 lux. Plants were three months old when the photographs and description were taken. In the following description, color references are made to The Royal Horticultural Society Colour Chart, 2015 Edition, except where general terms of ordinary dictionary significance are used.

Botanical classification: *Alstroemeria hybrida* 'ZAPRICHARMI'.

Parentage:

*Female, or seed, parent*.—Proprietary *Alstroemeria hybrida* selection identified as code number 72736-1, not patented.

*Male, or pollen, parent*.—Proprietary *Alstroemeria hybrida* selection identified as code number 94913-1, not patented.

Propagation:

*Type*.—In vitro rhizogenesis.

*Time to produce a rooted young plant, summer*.—About 40 days at temperatures of 16° C. to 25° C.

*Time to produce a rooted young plant, winter*.—About 60 days at temperatures of 16° C. to 20° C.

*Root description*.—Fibrous, fleshy, thick; color, close to 155D.

*Rooting habit*.—Freely branching; medium density.

*Rhizomes*.—Shape: Elongate; rounded. Length: About 10 cm to 30 cm. Diameter: About 3 mm to 10 mm. Texture and luster: Smooth; matte. Color: Close to 155D.

Plant description:

*Plant and growth habit*.—Compact, upright to outwardly spreading and uniformly mounding plant habit; freely branching habit with about 15 lateral branches developing per plant, dense and bushy appearance; moderately vigorous growth habit; and moderate growth rate.

*Plant height*.—About 20 cm.

*Plant diameter* (*spread*).—About 36 cm to 38 cm.

Lateral branch description:

*Length*.—About 14 cm to 16 cm.

*Diameter*.—About 5 mm to 6 mm.

*Internode length*.—About 6 mm to 10 mm.

*Strength*.—Strong, flexible.

*Aspect*.—About 30° from vertical.

*Texture and luster*.—Smooth, glabrous; semi-glossy.

*Color, developing*.—Close to 138D.

*Color, developed*.—Close to 138C.

Leaf description:

*Arrangement*.—Alternate; simple.

*Length*.—About 8 cm to 10 cm.

*Width*.—About 1.5 cm to 2 cm.

*Shape*.—Lanceolate.

*Apex*.—Acute.

*Base*.—Cuneate.

*Margin*.—Entire.

*Texture and luster, upper surface*.—Moderately rugose, glabrous; semi-glossy.

*Texture and luster, lower surface*.—Ribbed, glabrous; matte.

*Aspect*.—Upright to horizontal, twisting.

*Venation pattern*.—Parallel.

*Color*.—Developing leaves, upper surface: Close to 141C. Developing leaves, lower surface: Close to 138C. Fully expanded leaves, upper surface: Close to 137A; venation, close to N144D. Fully expanded leaves, lower surface: Close to 137C; venation, close to 137C.

*Petioles*.—Length: About 1 cm to 2 cm. Diameter: About 5 mm. Texture and luster: Smooth, glabrous; matte. Strength: Moderately strong, flexible. Color, upper surface: Close to 145C. Color, lower surface: Close to N144D.

Flower description:

*Flower type and habit*.—Single cup-shaped flowers arranged in compound umbels; flowers face upright to outwardly; perianth segments separate; freely flowering habit with about six to eight flowers per inflorescence and about 200 to 220 flower buds and flowers developing per plant.

*Natural flowering season*.—Flowering continuous from the spring until the autumn in The Netherlands; early flowering habit, plants begin flowering about 90 days after planting.

*Fragrance*.—None detected.

*Flower longevity on the plant*.—About three weeks; flowers not persistent.

*Flower buds*.—Length: About 2 cm to 2.2 cm. Diameter: About 7 mm. Shape: Roughly ovoid. Texture and luster: Smooth, glabrous; matte. Color: Close to 150C with stripes, close to 143A.

*Umbel height*.—About 9 cm to 10 cm.

*Umbel diameter*.—About 11 cm to 13 cm.

*Flower diameter*.—About 4 cm by 4.5 cm.

*Flower depth*.—About 4.2 cm.

*Perianth*.—Arrangement: Six arranged in two whorls, each whorl with two lateral and one median segments. Inner perianth, lateral segments: Length: About 4.8 cm to 5 cm. Width: About 1.4 cm. Shape: Oblanceolate. Apex: Wishbone-shaped and acuminate. Base: Attenuate. Margin: Entire; undulate. Texture and luster, upper surface: Smooth, glabrous; semi-glossy. Texture and luster, lower surface: Ribbed; matte. Color, when opening, upper surface: Close to 155A; central venation and towards the apex, close to 136C. Color, when opening, lower surface: Close to 155A; central venation and towards the apex, close to 141B. Color, fully opened, upper surface: Proximally and distally, close to N155D; mid-section, close to 2D; towards the apex, close to 136C; few stripes, close to 162B; color does not change with development. Color, fully opened, lower surface: Close to 155A; central venation and towards the apex, close to 141B; color does not change with development. Inner perianth, median segment: Length: About 4.6 cm. Width: About 1.4 cm. Shape: Oblanceolate. Apex: Wishbone-shaped and acuminate. Base: Attenuate. Margin: Entire; undulate. Texture and luster, upper surface: Smooth, glabrous; semi-glossy. Texture and luster, lower surface: Ribbed; matte. Color, when opening and fully opened, upper surface: Close to 155A; central venation and towards the apex, close to 136C; color does not change with development. Color, when opening and fully opened, lower surface: Close to 155A; central venation and towards the apex, close to 141B; color does not change with development. Outer perianth, lateral segments: Length: About 4.7 cm to 4.8 cm. Width: About 2.3 cm to 2.5 cm. Shape: Obovate. Apex: Embedded point. Base: Attenuate. Margin: Entire; undulate. Texture and luster, upper surface: Smooth, glabrous; semi-glossy. Texture and luster, lower surface: Ribbed; matte. Color, when opening, upper surface: Close to 155A; central venation and towards the apex, close to 136C. Color, when opening, lower surface: Close to 155A; central venation and towards the apex, close to 141B. Color, fully opened, upper surface: Close to N155D; central venation and towards the apex, close to 136C; color does not change with development. Color, fully opened, lower surface: Close to N155D; central venation and towards the apex, close to 141B; color does not change with development. Outer perianth, median segment: Length: About 4.7 cm to 4.8 cm. Width: About 2.3 cm to 2.5 cm. Shape: Obovate. Apex: Embedded point. Base: Attenuate. Margin: Entire; undulate. Texture and luster, upper surface: Smooth, glabrous; semi-glossy. Texture and luster, lower surface: Ribbed; matte. Color, when opening, upper surface: Close to 155A; central venation and towards the apex, close to 136C. Color, when opening, lower surface: Close to 155A; central venation and towards the apex, close to 141B. Color, fully opened, upper surface: Close to N155D; central venation and towards the apex, close to 136C; color does not change with development. Color, fully opened, lower surface: Close to N155D; central venation and towards the apex, close to 141B; color does not change with development.

*Pedicels*.—Length: About 1.5 cm. Diameter: About 1.5 mm. Strength: Strong. Angle: About 25° from vertical. Texture and luster: Smooth, glabrous; semi-glossy. Color: Close to 138B to 138C.

*Reproductive organs*.—Stamens: Quantity per flower: Typically six, partially deformed. Filament length: About 2 cm. Filament color: Close to N155D. Anther length: About 1.5 mm to 2 mm. Anther width: About 1 mm. Anther shape: Broadly elliptic. Anther color: Close to 4A. Pollen amount: Scarce. Pollen color: Close to 13A. Pistils: Quantity per flower: One. Pistil length: About 2.5 cm. Style length: About 2.5 cm. Style color: Close to N155D. Stigma diameter: About 3 mm. Stigma shape: Three-parted. Stigma color: Close to N155D. Ovary color: Close to 138A.

*Fruits and seeds*.—To date, fruit and seed development have not been observed on plants of the new *Alstroemeria*.

Pathogen & pest resistance: To date, plants of the new *Alstroemeria* have not been observed to be resistant to pathogens and pests common to *Alstroemeria* plants.

Garden performance: Plants of the new *Alstroemeria* have been observed to have excellent garden performance and to tolerate wind, rain, temperatures from about −5° C. to about 40° C. and to be suitable for USDA Hardiness Zone 9.

It is claimed:

1. A new and distinct *Alstroemeria* plant named 'ZAPRICHARMI' as illustrated and described.

* * * * *